（12） United States Patent
Wilmer et al.

(10) Patent No.: US 7,402,440 B2
(45) Date of Patent: Jul. 22, 2008

(54) PROPORTIONING SYSTEM AND PROCESS FOR OPERATING A PROPORTIONING SYSTEM

(75) Inventors: Jens Wilmer, Ahrensburg (DE); Ranier Rothhoff, Hamburg (DE)

(73) Assignee: Eppendorf AG, Hamburg (DE)

( * ) Notice: Subject to any disclaimer, the term of this patent is extended or adjusted under 35 U.S.C. 154(b) by 808 days.

(21) Appl. No.: 10/783,732

(22) Filed: Feb. 20, 2004

(65) Prior Publication Data

US 2004/0166027 A1 Aug. 26, 2004

(30) Foreign Application Priority Data

Feb. 20, 2003 (DE) ................. 103 07 030

(51) Int. Cl.
*G01N 1/10* (2006.01)
(52) U.S. Cl. ............... 436/180; 422/100; 347/20; 347/50; 347/116
(58) Field of Classification Search ........... 422/100; 347/20, 50, 116; 700/254; 436/180
See application file for complete search history.

(56) References Cited

U.S. PATENT DOCUMENTS

| | | | |
|---|---|---|---|
| 5,139,744 A | 8/1992 | Kowalski | 422/67 |
| 6,685,296 B2* | 2/2004 | Mochizuki et al. | 347/19 |
| 6,740,295 B2* | 5/2004 | Braun et al. | 422/100 |
| 6,841,129 B2* | 1/2005 | Braun et al. | 422/100 |
| 7,125,100 B2* | 10/2006 | Ishizawa et al. | 347/50 |
| 2002/0006362 A1* | 1/2002 | Ohta et al. | 422/102 |
| 2002/0180823 A1* | 12/2002 | Shinada et al. | 347/19 |
| 2005/0118069 A1* | 6/2005 | Solotareff et al. | 422/100 |
| 2006/0250446 A1* | 11/2006 | Wanibe et al. | 347/50 |

FOREIGN PATENT DOCUMENTS

| | | |
|---|---|---|
| DE | 38 83 267 T2 | 4/1994 |
| DE | 10117064 | 2/2003 |
| WO | 92/17231 | 10/1992 |
| WO | 01/62322 A1 | 8/2001 |

* cited by examiner

*Primary Examiner*—Brian R. Gordon
(74) *Attorney, Agent, or Firm*—Vidas, Arrett & Steinkraus, P.A.

(57) ABSTRACT

A proportioning system, comprising at least one tool, a programmable electronic storage device disposed on the tool, a proportioning device including a device for releasably mounting the tool, a device for actuating the tool, and a device for controlling of the device for actuating the tool and/or device for releasably mounting it, and a device for contacting connected to the device for controlling and disposed on the proportioning device and another device for contacting disposed on the tool that is connected to the programmable electronic storage device wherein the device for contacting and the other device for contacting contact each other when the tool is releasably mounted on the proportioning device.

4 Claims, 1 Drawing Sheet

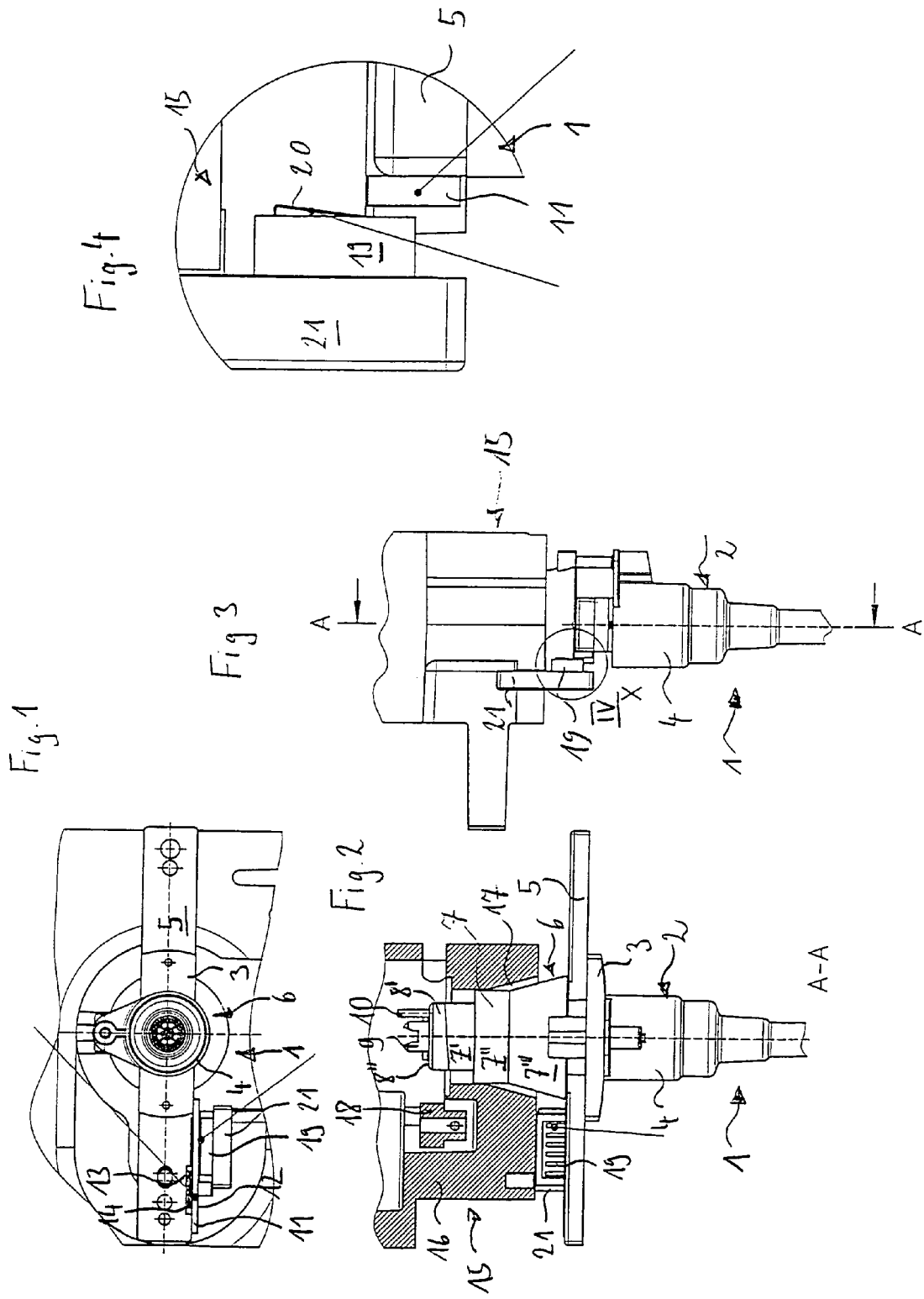

PROPORTIONING SYSTEM AND PROCESS FOR OPERATING A PROPORTIONING SYSTEM

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a proportioning system comprising at least one tool and a proportioning device and a process for operating a proportioning system using at least one tool and a proportioning device.

Proportioning systems, in the sense of this application, comprise manually or motor operated pipettes or dispensers of a portable or stationary design, automatic proportioning devices (LHS=Liquid Handling Stations), and laboratory-type automatic apparatuses (WS=Work Stations). These proportioning systems comprise at least one tool and a proportioning device. In many cases, the tool is a proportioning tool, e.g. a pipette tip, syringe or proportioning head, which has at least one receptacle to mount at least one pipette tip or syringe, or has one or more integrated proportioning needles. The proportioning device has a device for releasably mounting the tool, a device for actuating the tool, and a device for controlling the aforementioned devices. For example, the device for actuating comprises at least one piston-and-cylinder mechanism for displacing a column of air in the pipette tip. However, it can also be a device for mechanically actuating at least one a piston-and-cylinder mechanism which is integrated in a proportioning tool, e.g. in a syringe or proportioning head.

According to the German Patent Application 102 47 731.0, a conventional tool holder of laboratory-type automatic apparatus which has a prehensile tool can be employed to handle laboratory-type vessels, lids of vessels, and other objects. The invention integrates proportioning systems having a prehensile tool according to the German Patent Application 102 47 731.0.

When the tools are under manufacture data will be created which particularly comprise the order, the individual product number, and the date of manufacture. In addition, calibration data will be created by the manufacturer. For example, those are volume correction data for the individual calibration of proportioning tools. For example, those further are individual mechanical correction data which concern a misorientation of a proportioning or prehensile tool with respect to its seat in the proportioning device, for example.

Further, data of the tool may be created by the user. For example, those can be identification data, calibration data or data regarding its use (e.g. the number of type of uses).

The production-related data has been archived in documents accompanying the tool or by the manufacturer up to now. In some cases, the data is accessible only via information delivered by the manufacturer.

Conventionally, the application-related data are recorded by the user in accompanying documents. The disadvantage of the way the data has been handled hitherto is that it is troublesome to assign the data to the tools and to update and supplement it and that the data is not always readily available. Thus, for example, data of calibration has to be entered with difficulty to a laboratory-type automatic apparatus.

U.S. Pat. No. 5,139,744 has made known a laboratory-type automatic apparatus with an identification system for exchangeable proportioning modules. The proportioning modules have a non-digital electronic network element which is designed as a RC member for changing the tune of a resonant circuit. A pulse width variation is to be measured for identification. The RC member virtually helps only in permanently assigning a single information to a proportioning tool. Accordingly, an application is indicated for an identification of the proportioning tool.

DE 101 17 064 A1 describes a device for automatic dispensing which comprises a cartridge with a tank, a microproportioning element, and a clamping device as is shown in FIG. 1. According to FIG. 2, the cartridge is mounted on a clamping mechanism of an assembly head via the clamping device. The dispensing head formed in such a way is fixed to a dispensing head support as is shown in FIGS. 3, 4. The dispensing head is movable to a specimen slide, which is movable in an X-Y plane in a Z direction (possibly also in an X-Y plane). The cartridges are provided with an electrically readable code which is stored, for example, in an EEPROM, HF tag, bar code and the like. The code can contain fluid data, e.g. cartridge specific data such as substance identifiers, solvent identifiers, filling dates, aging, purity and the like. This data can be fed directly to test planning so that an optimum use or availability of substances is always ensured. Thus, when a cartridge is changed cartridge specific data makes it unnecessary for the operator to inform about the position to be loaded because this system is able to identify it automatically.

WO/01/62322 A1 relates to a microelectronic inhalation apparatus to administer aerosols. An aerosol container is provided with a microelectronic storage element. The container can be inserted in a receptacle which has an microelectronic assembly. When the container has been inserted into the receptacle a display of the microelectronic assembly displays information stored in the storage element.

WO 01/62322 A1 discloses a similar medicament dispenser in which the container or receptacle is equipped with a RFID.

DE 38 83 267 T2 relates to an article identification system with an ID device which can be mounted on an article requiring identification, and a read control device to read data from the an ID device. The article identification system serves for managing tools of a machine tool or components or products at a factory or for an identification of articles in a distribution and consignment system or the like.

BRIEF SUMMARY OF THE INVENTION

Accordingly, it is the object of the invention to provide a proportioning system with a tool and a proportioning device and a process for operating a proportioning system using a tool and a proportioning device where it is made easier to handle data of the tool.

Advantageous aspects of the proportioning system are indicated in the sub-claims.

The inventive proportioning system has at least one tool, a programmable electronic storage device disposed on the tool, a proportioning device including a device for releasably mounting the tool, a device for actuating the tool, and a device for controlling the device for actuating the tool and/or device for releasably mounting it, and a device for contacting connected to the device for controlling and disposed on the proportioning device and another device for contacting disposed on the tool that is connected to the programmable electronic storage device wherein the device for contacting and the other device for contacting contact each other when the tool is releasably mounted on the proportioning device.

During the manufacture of the tool of the inventive proportioning system, production-related data can be simply written into the programmable electronic storage device during the production process and, hence, can be documented and carried along directly on the tool. Specifically, manufacture-related quality check data for the calibration of the tools and mechanical correction data can be stored. Accordingly, application-related data can be simply written in while in application and, thus, can be documented directly on the tool. The clear and direct assignment and easy accessibility of the production-related and application-related data is ensured throughout the production process and application. The data stored in the programmable electronic storage device is taken into account by the device for controlling in controlling the device for actuation and/or the device for releasably mounting. It is preferred that calibration data and mechanical correction data are read out automatically in using a tool, e.g. in laboratory-type automatic apparatus, and are taken into account in operating the proportioning system. Later corrections of the calibration data and mechanical correction data subsequent to service or routine checks or corrections by users are possible.

The device for releasably mounting serves for releasably mounting the tool to the proportioning device.

The device for contacting serves for electrically contacting the other device for contacting when the tool is releasably fixed to the proportioning device. The device for controlling and the programmable electronic storage device are electrically interconnected via the device for contacting and the other device for contacting when the tool is releasably mounted to the proportioning device.

Thus, the transfer of data between the programmable electronic storage device and the device for controlling is accomplished via the devices for contacting. Production-related data and application-related data can also be written in via those devices. During manufacture, data can be written in via appropriate electronic data processing systems. This also is true for application. The user can also write in data via the device for controlling.

The proportioning device can be designed in different ways. In one aspect, the proportioning device is a pipette and/or dispenser or proportioning station (possibly comprising a pipette and/or dispenser) or a laboratory-type automatic apparatus (possibly comprising a pipette and/or dispenser) and/or is at least a tool, a pipette tip and/or syringe and/or a proportioning head and/or another proportioning tool and/or prehensile tool. For example, the proportioning head has one or more displacement devices for one or more pipette tips or a gearing for one or more syringes. The displacement device or the plurality of displacement devices or the gearing can be actuated by the device for actuating the proportioning device when the proportioning head is mounted on the proportioning device.

In one aspect, the device for contacting is a spring-loaded contact strip and the other device for contacting is a contact strip. This allows to ensure safe contacting under laboratory-scale conditions. The spring-loaded contact strip and the contact strip help in connecting a programmable electronic storage device having at least one common electronic semiconductor module to the device for controlling at a low expenditure. The spring-loaded contact strip and the contact strip have a beneficial self-cleaning effect. In one aspect, the contact strip is a printed circuit board with parallel conductor tracks which define the contacts. In one aspect, the spring contacts of the spring-loaded contact strip and/or the conductor tracks of the contact strip are plated with gold to achieve proper contacting via a multiplicity of cycles.

In one aspect, the devices for contacting and the other device for contacting, in addition to having contacts for a data transfer, have contacts for a power supply. Specifically, these contacts can be connected to the programmable electronic storage device or a driving device of a proportioning or prehensile tool to supply the said devices with current.

In one aspect, the programmable electronic storage device is an EEPROM. This allows a non-volatile storage of the data and to simply write in data or overwrite data which is written in during production or application.

In one aspect, the programmable electronic storage device is disposed between the contact strip and a casing wall of the tool. This makes it possible to accommodate the storage device in a protected manner.

In one aspect, the programmable electronic storage device is coated with a varnish. This protects the storage device. The varnish can specifically be an autoclavable varnish, which makes the entire tool autoclavable.

In one aspect, a device for releasably mounting on the proportioning device has an axial receptacle and the tool has a spigot for introduction into the receptacle.

Advantageously, the device for releasably mounting and the tool are configured as is described in the German Patent Application 102 47 731.0 the contents of which is incorporated by reference here.

In one aspect, the spring contacts and the contact strip are oriented in parallel with the direction of assembly for the proportioning device and the tool. The parallel orientation ensures safe contacting when the tool and proportioning device are releasably connected.

In one aspect, production-related and/or application-related data can be stored in the programmable electronic storage device. The invention also includes the storage of exclusively production-related data or the storage of exclusively application-related data or the storage of production-related and application-related data.

In the process for operating a proportioning system using at least one tool and a proportioning device, production-related data is stored during production and/or application-related data is stored during application in a programmable electronic storage device of the tool, the production-related data and/or application-related data is read out from the programmable electronic storage device and is supplied to a device for controlling comprised in the proportioning device during application, and the device for controlling controls a device comprised in the proportioning device for actuating the tool and/or a device comprised in the proportioning device for releasably mounting the tool on the proportioning device in dependence on the production-related data and/or application-related data.

In one aspect, the production-related data and/or application-related data is calibration data and/or mechanical correction data. The calibration data and/or mechanical correction is are particularly used for the precise control of proportioning volumes and/or device functions.

In one aspect, the production-related and/or application-related data are written into the programmable electronic storage device by means of an electronic data processing system separated from the proportioning system. For example, this is a PC as used in a production or laboratory area.

In one aspect, the production-related and/or application-related data are written into the programmable electronic storage device or are read out therefrom by means of the device for controlling and/or an electronic data processing device comprised in the proportioning system. For example, the device for controlling and/or the electronic data processing device is a microcomputer.

In one aspect, the production-related and/or application-related data is written into or read from the programmable electronic storage device via a device for contacting the proportioning device and another contacting device contacting it and connected thereto, which is connected to the data processing device comprised in the proportioning system and/or to the device for controlling.

BRIEF DESCRIPTION OF THE SEVERAL VIEWS OF THE DRAWINGS

The invention will be described in more detail below with reference to the accompanying drawing of an embodiment. In the drawings:

FIG. 1 shows a tool in a bottom view

FIG. 2 shows the tool as inserted in a tool holder of a laboratory-type automatic apparatus in a vertical partial section;

FIG. 3 shows the tool as inserted in a tool holder in a side partial section;

FIG. 4 shows the enlarged detail IV of FIG. 3.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated The proportioning tool illustrated in the drawing and the tool holder substantially correspond to the proportioning tool illustrated with reference to FIGS. 4 to 6 and the tool holder described with reference to FIGS. 7 and 10 for a laboratory-type automatic apparatus according to the German Patent Application 102 47 731.0 which is also incorporated by reference here.

The proportioning tool 1 has a bottom component 2 with a base plate 3 from which a cylinder and a slip-on cone connected thereto for a pipette tip projects downwards, which cannot be seen in the drawing. The cylinder has slidably guided therein a piston, which cannot be seen either. A throw-off sleeve 4 which can be actuated from above to press a pipette tip off the cone extends around the piston-and cylinder assembly.

A mounting plate 5 which substantially is stripe-shaped is fixed to the top of the base plate 3.

An upper part 6 which has a hollow mounting spigot 7 is disposed on top of the mounting plate 5. The spigot has an upper cylindrical portion 7' which has two claws 8', 8" at the outer circumference to define a bayonet lock component. The claws 8', 8" have a slight thread lead to lock a bayonet joint.

Further, the spigot 7 has a central cylindrical portion 7" with a larger outer diameter than that the upper cylindrical portion 7' and a lower portion 7''' which conically widens downwards.

The spigot 7 has protruded therefrom a carrier dog 9 which, in a rotationally fixed manner, is connected to a worm gear spindle (not shown) which is rotatable within the proportioning tool 1 in a threaded nut which can be displaced on radial projections in longitudinally directed groves within the proportioning tool 1. The threaded nut is connected to the piston.

Consequently, the piston is displaceable within the cylinder by rotating the carrier dog 9. This allows to displace a column of air to draw a liquid into or out of a pipette tip on the slip-on cone.

The spigot 7 has protruded therefrom an axially directed cylindrical pin 10 which is connected to the threaded nut to indicate its position and, hence, the position of the piston in the cylinder.

The side of the mounting plate 5 has fixed thereto a contact strip 11 in the form of a printed circuit board the outside of which has several contacts 12 which are define by conductor paths. They are coated with gold. The mounting plate 5 has a recess 13 below the contact strip 11. The recess has disposed therein an EEPROM mounted on the inside of the printed circuit board 11.

Some or all contacts 12 of the contact strip 11 are electrically connected to a contact terminal pin of the EEPROM.

The tool holder 15 has a base component 15 which has a cylindrical receptacle 17 at bottom. The proportioning head 1 with a mounting spigot 7 can be inserted therein. The receptacle 16 is contoured accordingly.

Within the base component 16, a pinion 18 is disposed which is connected to the shaft of an electric driving motor, which is not shown, in order to drive a bayonet locking ring, which is not shown either, which can be connected to the mounting spigot 7. The drive for the carrier dog 9 and the sensor for sensing the cylindrical pin 10 are not shown either.

The underside of the base component 16 has mounted thereon a spring-loaded contact strip 19 with gold-plated spring contacts 20. For this purpose, a mounting plate 21 is fixed to the side of the base component 16. The spring-loaded contact strip 19 is connected to an electronic device, which is not shown, for controlling the laboratory-type automatic apparatus. For example, this can be a microcontroller or PC.

When the proportioning tool is inserted into the tool holder 15 and is releasably connected thereto the spring-loaded contact strip 19 contacts the contact strip 11. The data stored in the EEPROM can then be read out by the electronic device for controlling. Read-out calibration data and data concerning mechanical tolerances can be taken into account by the electronic device in controlling proportioning procedures and in moving the tool holder 15.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A process for operating a proportioning system comprising the steps of:
providing a proportioning system, the proportioning system, comprising at least one tool, a programmable electronic storage device disposed on the tool, a proportioning device including a device for releasably mounting the tool, a device for actuating the tool, and a controlling device for actuating the tool and/or for releasably mounting it, and a first contacting device connected to the device for controlling it and disposed on the proportioning device and a second contacting device for contacting disposed on the tool that is connected to the programmable electronic storage device, wherein the first contacting device and second contacting device contact each other when the tool is releasably mounted on the proportioning device,
and storing production-related data and/or application-related data, wherein:
the production-related data is stored during production and/or application-related data is stored during application in the programmable electronic storage device of the tool, the production-related data and/or application-related data is read from the programmable electronic storage device and is supplied to a controlling device comprised in the proportioning device during application, and the controlling device controls a device comprised in the proportioning device for actuating the tool and/or a device comprised in the proportioning device for releasably mounting the tool on the proportioning device in dependence on the production-related data and/or application-related data and wherein the production-related data and/or application related data are calibration data and/or mechanical correction data.

2. The process according to claim 1 wherein the production-related and/or application-related data are written into the programmable electronic storage device by means of an electronic data processing system separated from the proportioning system.

3. The process according to claim 1 wherein the production-related and/or application-related data are written into the programmable electronic storage device or are read therefrom by means of the device for controlling and/or an electronic data processing device comprised in the proportioning system.

4. The process according to claim 1 wherein the production-related and/or application-related data are written into or read from the programmable electronic storage device via the first contacting device and the second contacting device contacting it and connected thereto, which is connected to the data processing device comprised in the proportioning system and/or to the device for controlling.

* * * * *